(12) United States Patent
Jewett et al.

(10) Patent No.: US 6,223,746 B1
(45) Date of Patent: *May 1, 2001

(54) METERED DOSE INHALER PUMP

(75) Inventors: Warren R. Jewett, Cary; Robert C. Williams, III, Raleigh, both of NC (US)

(73) Assignee: IEP Pharmaceutical Devices Inc., Raleigh, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/022,984

(22) Filed: Feb. 12, 1998

(51) Int. Cl.[7] .......................... A61M 15/00; A61M 16/10
(52) U.S. Cl. .............................. 128/203.12; 128/200.14; 128/200.22; 222/82; 222/450; 222/534
(58) Field of Search .................. 128/200.23, 200.18, 128/200.21, 200.14, 203.12, 203.15, 200.22; 222/144, 149, 325, 345, 82, 83, 450, 534, 380, 387; 11/11

(56) References Cited

U.S. PATENT DOCUMENTS

| | | | |
|---|---|---|---|
| 3,739,950 | * 6/1973 | Gorman | 222/534 |
| 3,921,637 | * 11/1975 | Bennie et al. | 128/203.15 |
| 4,017,007 | * 4/1977 | Riccio | 222/80 |
| 4,130,116 | * 12/1978 | Cavazza | 128/200.14 |
| 4,534,345 | 8/1985 | Wetterlin . | |
| 4,796,614 | * 1/1989 | Nowacki et al. | 128/200.14 |
| 5,221,025 | 6/1993 | Privas . | |
| 5,497,944 | * 3/1996 | Weston et al. | 239/321 |
| 5,515,842 | * 5/1996 | Ramseyer et al. | 128/200.18 |
| 5,617,845 | * 4/1997 | Poss et al. | 128/203.15 |
| 5,662,271 | * 9/1997 | Weston et al. | 239/321 |
| 5,934,510 | * 8/1999 | Andersen | 222/83 |

* cited by examiner

Primary Examiner—John G. Weiss
Assistant Examiner—Joseph F. Weiss, Jr.
(74) Attorney, Agent, or Firm—Pitney, Hardin, Kipp & Szuch, LLP

(57) ABSTRACT

A metered dose inhaler pump for delivering a metered dose of an active compound from an active compound inlet through a spray outlet without the need of a pressurized active compound container. Reciprocating action of an inlet valve, an outlet valve and a plunger alternately draw a metered dose of the active compound from an active compound container into an active compound chamber and pressurize the drawn metered dose of the active compound to eject the metered dose through the spray outlet. The plunger substantially fills and evacuates the metered dose chamber, leaving no void head space therein.

31 Claims, 7 Drawing Sheets

METERED DOSE INHALER PUMP

BACKGROUND OF THE INVENTION

1. Field of the Invention

The present invention relates to metered dose inhalers, and, more particularly, to a pump for a metered dose inhaler which does not require the use of a pressurized container of medicine.

2. Brief Description of Related Art

Metered dose inhalers have been commercially available for use in the treatment of a variety of respiratory ailments, such as asthma. Such metered dose inhalers typically require a pressurized cylinder or canister of medicine to deliver a metered dose of such medicine to a person's respiratory tract. These pressurized cylinders or canisters have employed a halogenated hydrocarbon as a propellant, with the active compound dissolved in the propellant or suspended in the propellant in solid, micronized form.

For example, U.S. Pat. No. 4,955,371 describes a disposable inhalation device wherein an aerosol measured dose canister provides a short spray for releasing a fixed dose of medicine. However, environmental concerns have disfavored the use of halogenated hydrocarbons in aerosol containers. U.S. Pat. No. 4,534,345 describes a dosage inhaler employing a dosing unit for dosing a pharmacologically active compound separate from a pressurized propellant container. The pressurized container contains liquified, pressurized carbon dioxide. In either case, the propellant is delivered into a person's respiratory tract with the medicine dose.

Thus, there is a need for a metered dose inhaler capable of delivering a metered dose of an active compound without the use of a pressurized propellant. Therefore, in order to alleviate these and other problems, an objective of the present invention is to provide a metered dose inhaler pump for pressurizing and delivering a metered dose of an active compound to a person's respiratory tract.

SUMMARY OF THE INVENTION

The above and other beneficial objects are obtained in accordance with the present invention by providing a metered dose inhaler pump having an active compound inlet for drawing a metered dose of a pharmacologically active compound from an unpressurized container into a metered dose chamber and a spray outlet for delivering the active compound from the metered dose chamber into a person's respiratory tract. A first valve is provided at the inlet, and a second valve is provided at the outlet. The metered dose chamber is provided between and in fluid communication with the first valve and the second valve. A spring-loaded trigger urges a plunger into the metered dose chamber, closing the first valve, opening the second valve and filling and evacuating the metered dose chamber, thereby delivering the metered does of the active compound from the metered dose chamber to a person's respiratory tract through the outlet.

DETAILED DESCRIPTION OF THE PREFERRED EMBODIMENTS

Figure 1:
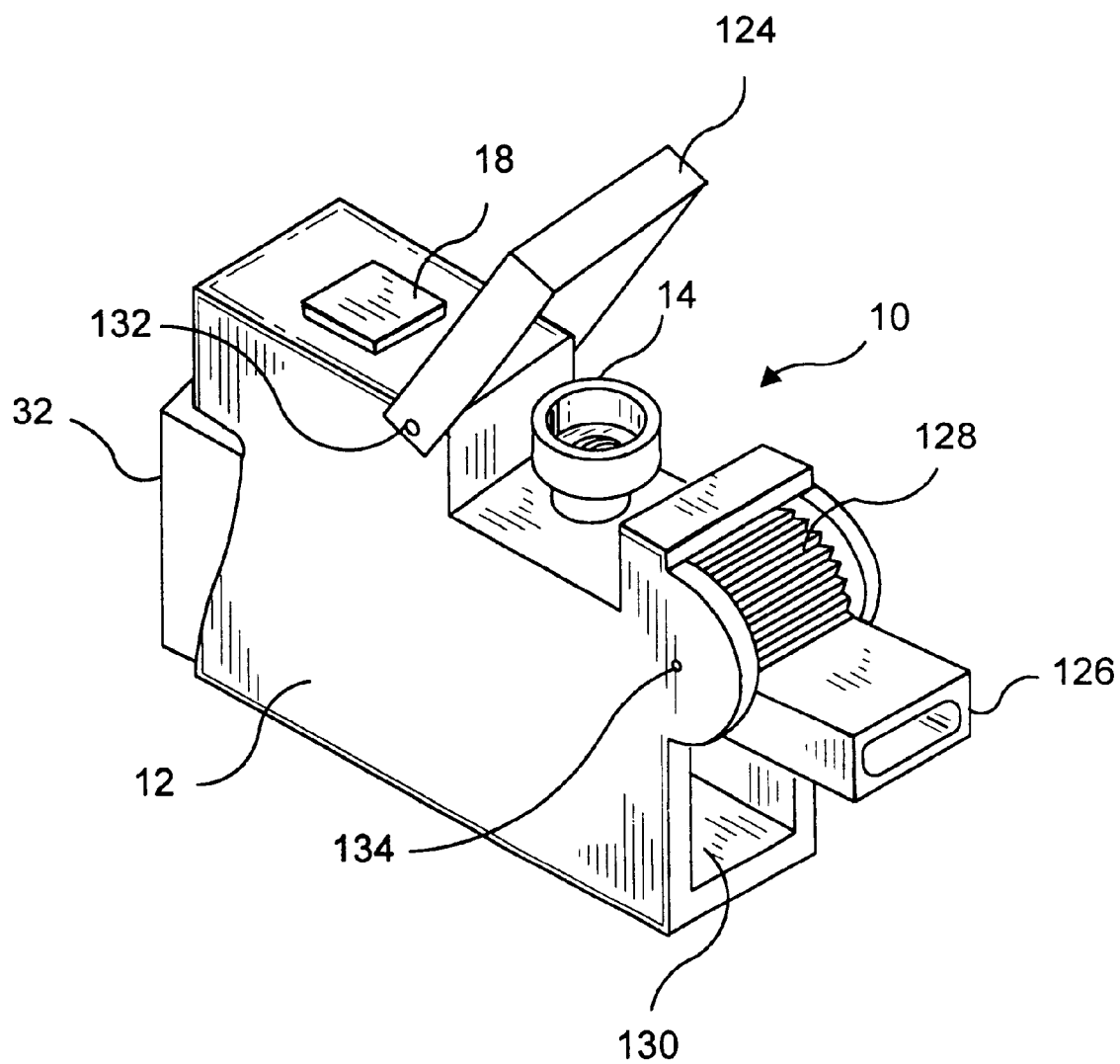
FIG. 1 is a front perspective view of a metered dose inhaler pump according to the present invention.

Those skilled in the art will gain an appreciation of the invention when viewed with the accompanying drawings of FIGS. 1–7, inclusive. The individual reference characters designate the same or similar elements throughout the several drawings.

FIG. 1 is a front perspective view of a metered dose inhaler pump 10. Metered dose inhaler pump 10 includes a housing 12 having an active compound inlet 14, a spray nozzle 16, a trigger 18 and a cocking trigger 32. Housing 12 is in the form of a shell having a first shell half 22 and a second shell half 24. First shell half 22 and second shell half 24 have mirror-image internal structures, which will be described in detail below. First shell half 22 and second shell half 24 are joined by ultrasonic bonding. First shell half 22 and second shell half 24 may be made of any suitable material. However, a plastic material is preferred because of its light weight and manufacturing characteristics.

Figure 2:
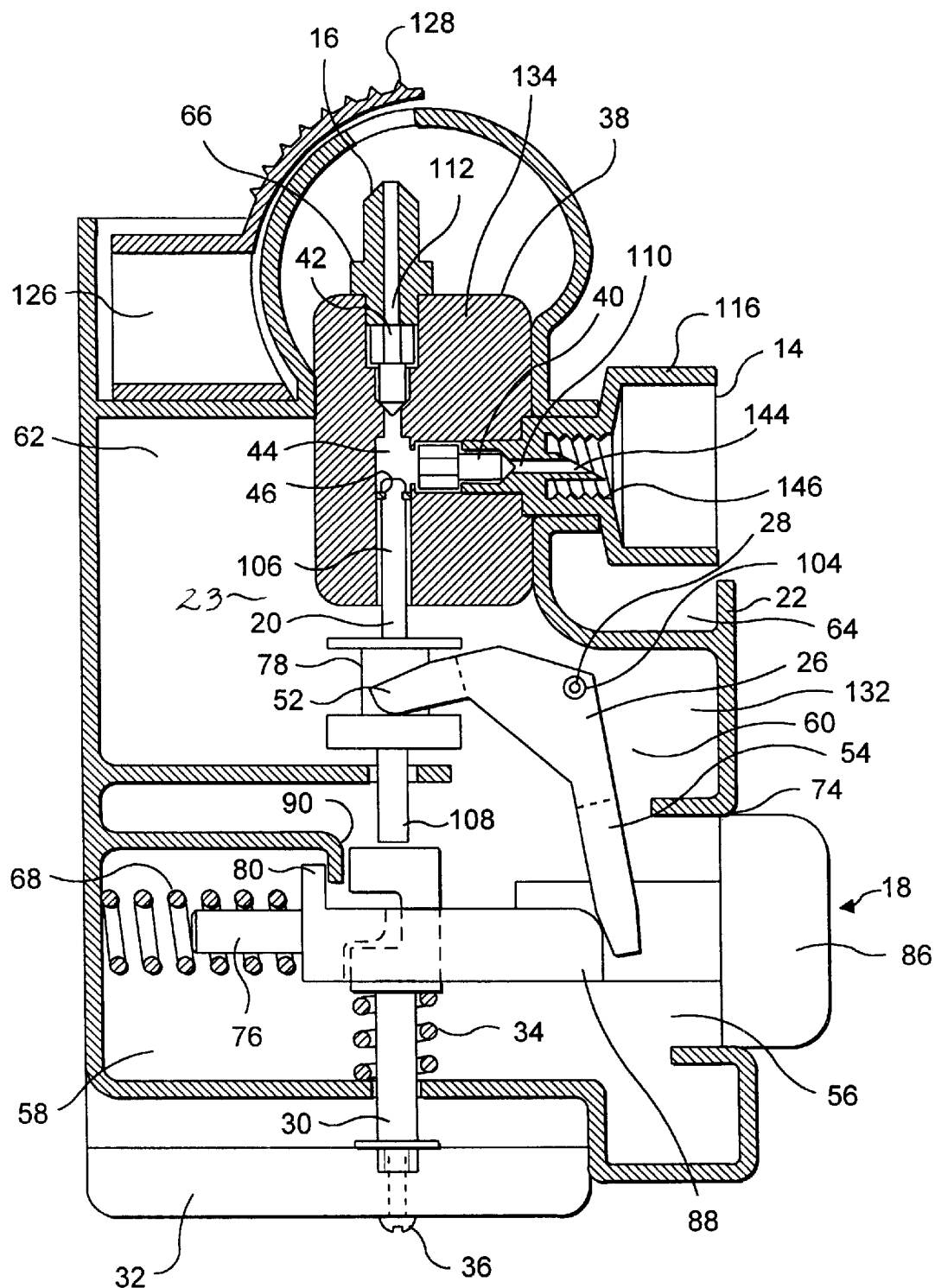
FIG. 2 is a front sectional view of the metered dose inhaler pump.

Cover 124 is mounted onto housing 12 rotatably about pin 132. Cover 124 can be opened and closed by the user of metered dose inhaler 10 to selectively expose active compound inlet 14 for receiving the canister of active compound, not shown. Cover 124 may be formed of a clear plastic material or may include a clear window for allowing a user to visually determine the number of metered doses remaining in the active compound container. Mouthpiece 126 is mounted in housing 12 rotatably about pin 134. Mouthpiece 126 is adapted by size and configuration for insertion into the oral cavity of a person and to couple or sealingly engage with the oral lips for inspiration and expiration of the breath of the person. Alternatively, mouthpiece 126 can be adapted to engage with the person's nasal passages. Serrations 128 are provided on the body of mouthpiece 126 to facilitate the rotation of mouthpiece 126 about pin 134. A pocket 130 is formed in housing 12 so that mouthpiece 126 can be rotated to a closed position, wherein the top surface of mouthpiece 126 as shown in FIG. 2 becomes flush with housing 12. When both cover 124 and mouthpiece 126 are in their closed positions, metered dose inhaler 10 forms a compact and easily carried and stored device, and mouthpiece 126 and active compound inlet 14 are protected from contaminants and physical damage.

Now referring to FIG. 2, the internal structure of first shell half 22 disclosing structure of pump 23 is described in detail. It will be understood that the description of the internal structure of first shell half 22 necessarily describes the internal structure of second shell half 24 by virtue of second shell half 24 being a mirror image of first shell half 22. First shell half 22 has wall members defining a trigger channel 56, a linkage channel 60, a valve channel 62, an inlet channel 64, and an outlet channel 66 for respectively receiving trigger 18, linkage 26, valve block 38, active compound inlet 14 and spray outlet 16.

Trigger 18 is received in housing 12 by trigger channel 56. Trigger 18 has a shaft portion 88, a button portion 86 at a proximal end of shaft portion 88 and a spring guide 76 at a distal end of shaft portion 88. A helical spring 68 is provided to bias trigger 18 outwardly from housing 12, and, more specifically, to bias button portion 86 outwardly from opening 74. One end of spring 68 is urged against the blind end of trigger channel 56, the other end is received by spring guide 76 protruding from distal end of trigger 18. Spring guide 76 is provided for maintaining proper orientation of spring 68. A lip 80 is provided generally near the distal end of shaft portion 88 for engaging with a detent 90 of trigger channel 56 to counteract the action of spring 68 and to maintain trigger 18 within housing 12.

Figure 4:
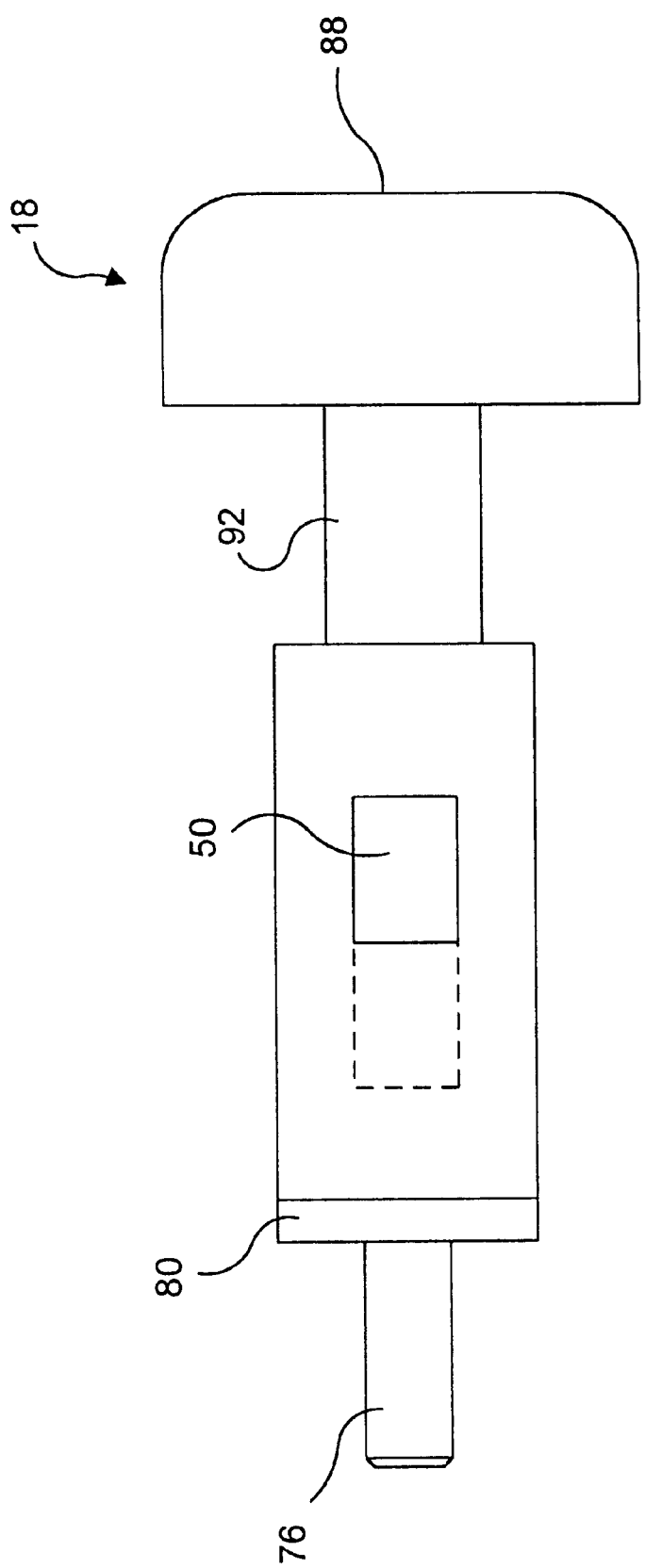
FIG. 4 is a top plan view of a trigger of the metered dose inhaler pump.

Now referring to FIG. 4 the further structure of trigger 18 will be described in detail. FIG. 4 is a top view of trigger 18, which illustrates that shaft portion 88 includes a step portion 92 of decreased width where shaft portion 88 extends from button portion 86. Button portion 86 is shown with a generally square shape. It will be appreciated that button portion 86 may have any shape. A channel 50 is provided in shaft portion 88 generally located centrally along the length of shaft 88 between step portion 92 and lip 80. Channel 50 is provided to receive cocking arm 30 as will be described below. Trigger 18 may be made of any suitable material. However, trigger 18 is preferably made of a plastic material, which is preferred because of the relatively light weight and ease of manufacturing plastic materials.

Now referring to FIG. 5 the structure of cocking arm 30 will be described in detail. Cocking arm 30 is disposed within cocking arm channel 58 and has a block portion 94 and a shank portion 96 extending from block portion 94 and terminating at a head portion 98. Head portion 98 includes an internally threaded hole 100 for receiving screw 36 and protrudes through housing 12 through channel 58. The diameter of head portion 98 is larger than that of shank portion 96 so that head portion 98 prevents cocking arm 30 from completely entering housing 12. Head portion 98 may be integrally formed with cocking arm 30 or head portion 98 may be separately manufactured and screwed onto the end of shank portion 96. Block portion 94 has a width that will permit block portion 94 to be slippingly fitted into channel 50 of trigger 18 and has a generally U-shaped channel 102 for allowing trigger 18 to slide perpendicularly to cocking arm 30 as will be described below. Cocking arm 30 may be made of any suitable material. However, cocking arm 30 is preferably made of aluminum or an alloy thereof because of its material and manufacturing characteristics.

Figure 5:
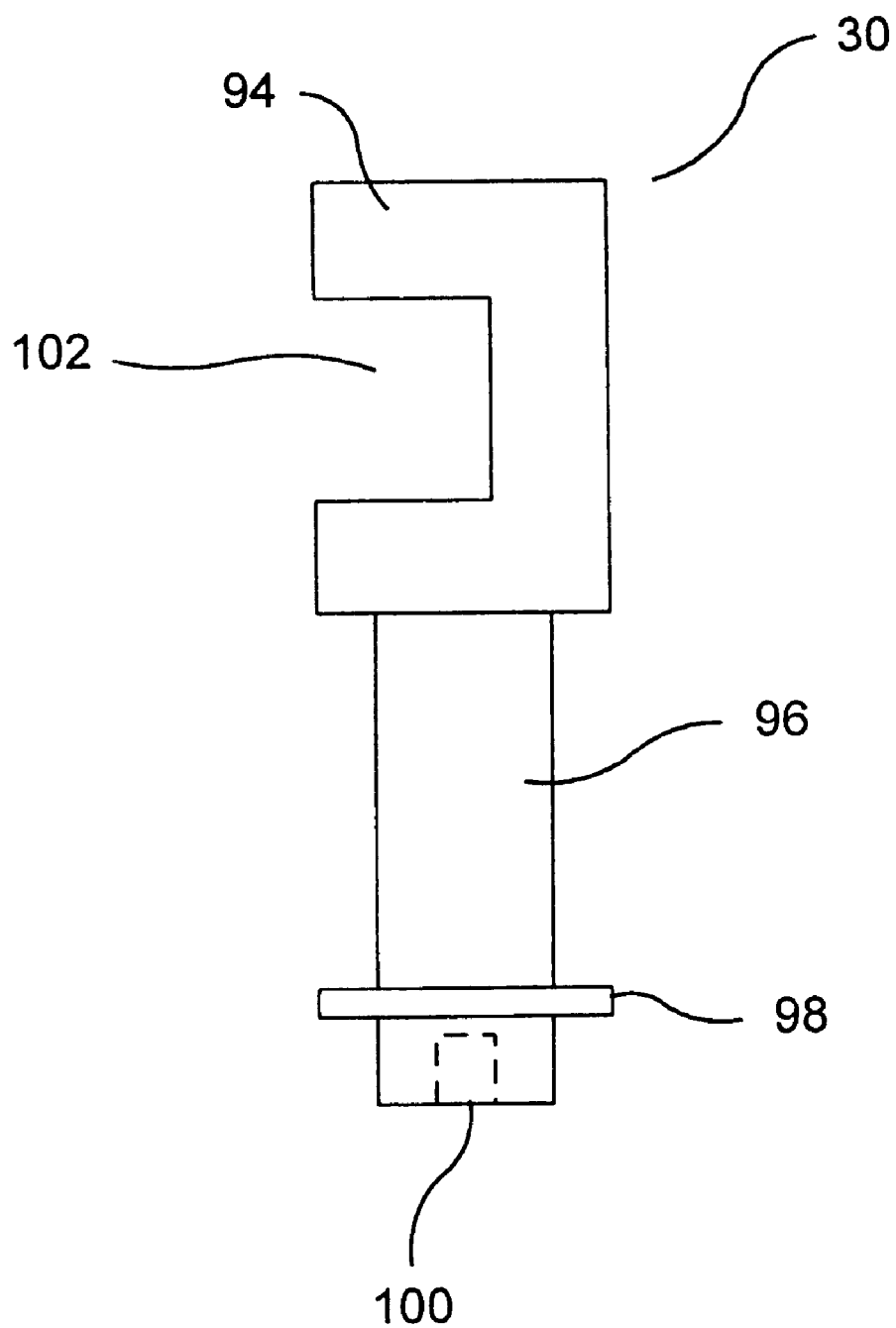
FIG. 5 is a front elevational view of a cocking arm of the metered dose inhaler pump.

Now referring to FIG. 2, a helical spring 34 is disposed along the length of shank portion 96 so that one end of spring 34 is urged against block portion 94, illustrated in FIG. 5, and the other end of spring 34 is urged against the end of cocking channel 58. Spring 34 acts to bias cocking arm 30 inwardly into housing 12, as illustrated in FIG. 1. The proximal end of shank 96 has an internally threaded hole 100 for receiving screw 36 for attaching cocking trigger 32 thereto.

Linkage 26 is disposed within housing 12 in linkage channel 60. First shell half 22 has a hole, not shown, and linkage has a hole 104 for receiving pin 28 about which linkage 26 is rotatable. Linkage 26 is generally L-shaped having a first leg 52 and a second leg 54. Each leg 52, 54 has a U-shaped channel for respectively receiving seat 78 of plunger 20 and step 92 of trigger 18. Linkage may be made of any suitable material but is preferably made of aluminum or an alloy thereof for its material and manufacturing characteristics.

Plunger 20 is a generally cylindrical member having seat 78 disposed along the length thereof. A distal end of plunger 20 defines a shank 106, and a proximal end of plunger 20 defines a head 108, shank 106 and head 108 being separated by seat 78. Plunger may be integrally formed. Alternatively, seat 78 may be formed as a distinct portion thereof and mounted on shank 106. Plunger 20 may be made of any suitable material but is preferably made of stainless steel or an alloy thereof for its material and manufacturing characteristics. Shank channel 114 should have a surface finish in accordance with the surface finish requirements of seal 46.

Figure 3:
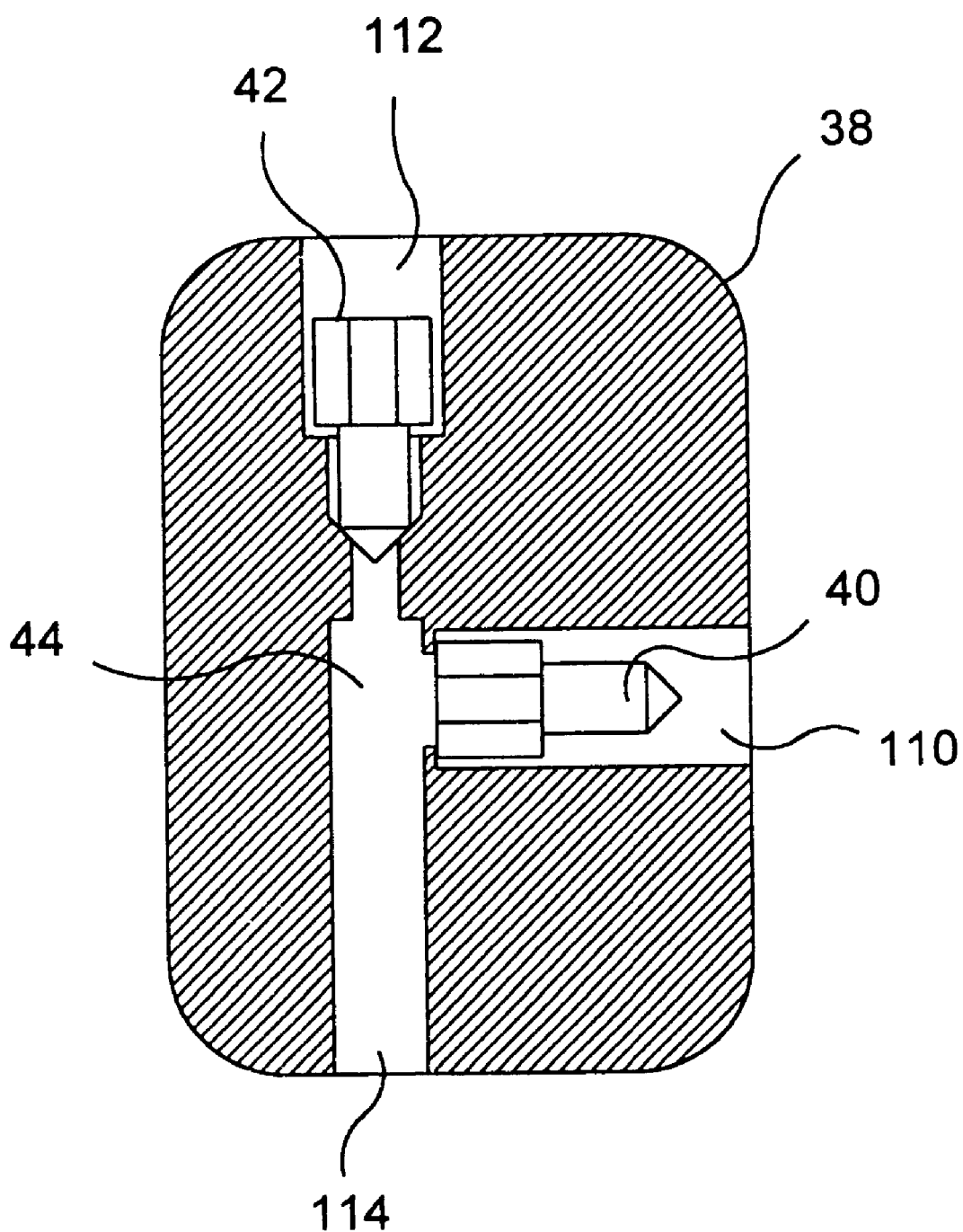
FIG. 3 is a front sectional view of a valve block of the metered dose inhaler pump.
Figure 6:
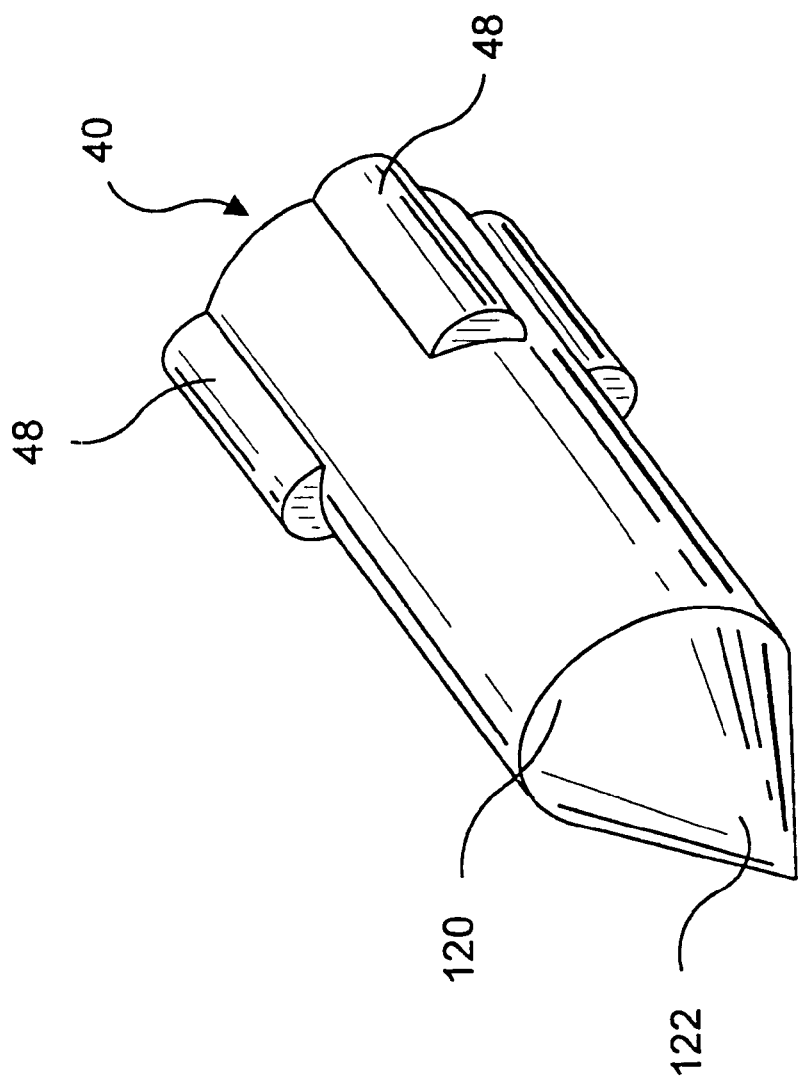
FIG. 6 is a perspective view of an inlet valve of the metered dose inhaler pump.

Now referring to FIG. 3, the internal structure of valve block 38 is described in detail. Valve block 38 is disposed within valve channel 62 of housing 12 and its position is fixed thereby. Valve block 38 has a shank channel 114 for receiving shank portion 106 of plunger 20, an inlet valve channel 110, an outlet valve channel 112 and a metered dose chamber 44. A seal 46 is provided in a seat along the length of shank 106 to form a fluid-tight seal between shank 106 and metered dose chamber 44. An inlet valve 40 is provided within inlet valve channel 110, and an outlet valve 42 is provided within outlet valve channel 112. Inlet valve has a generally cylindrical body 120 of substantially the same diameter as inlet valve channel 110 and a conical tip 122. FIG. 6 illustrates the preferred configuration of inlet valve 40. Fins 48 are provided along the length of the body 120 of inlet valve 40. Inlet valve 40 may be made of any suitable material but is preferably made of a resilient material to ensure fluid-tight sealing. More specifically, inlet valve 40 is made of a silicone elastomer. The resiliency of inlet valve 40 permits inlet valve 40 to act both as a sealing member and as a spring. Inlet valve 40 is provided with a plurality of fins 48 to maintain inlet valve 40 centrally positioned within inlet valve channel 110, while permitting fluid flow between fins 48 at a low resistance.

Figure 7:
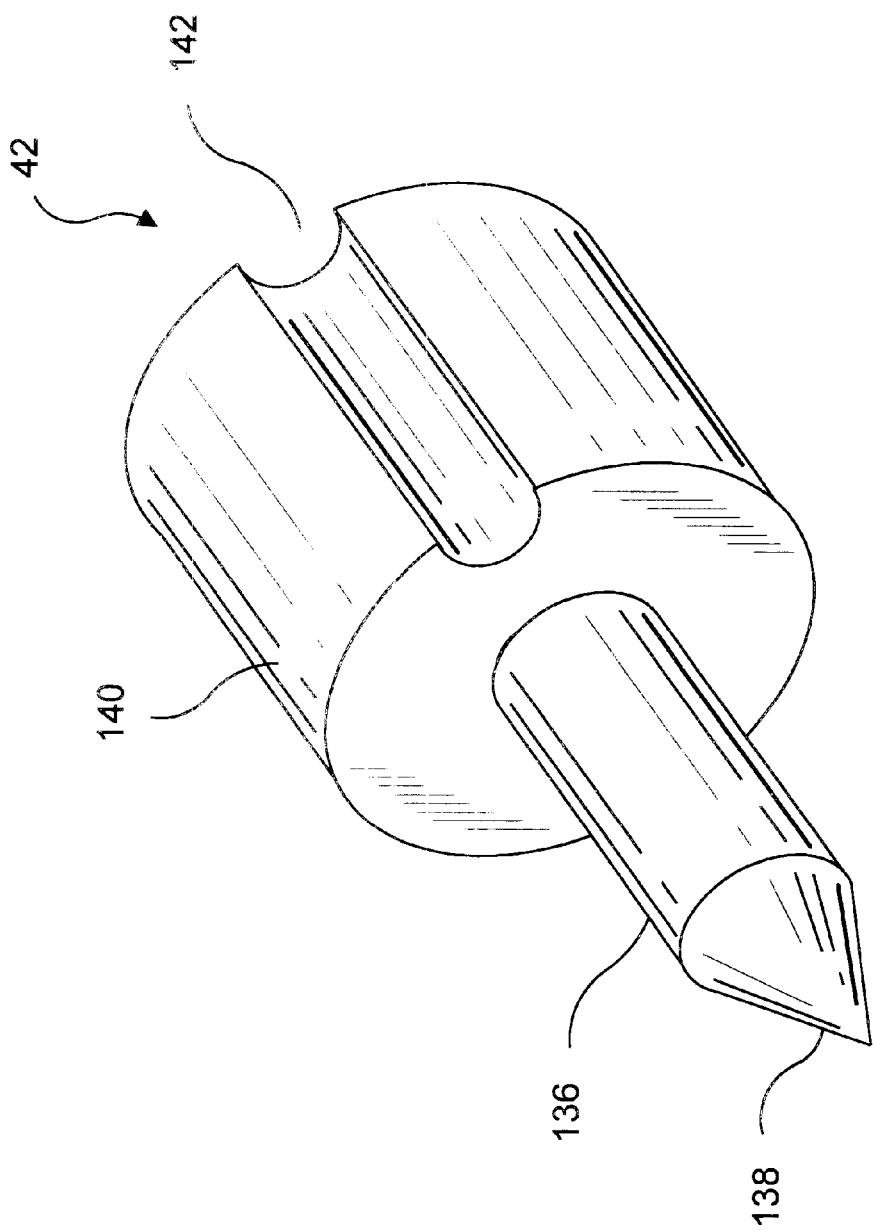
FIG. 7 is a perspective view of an outlet valve of the metered dose inhaler pump.

FIG. 7 illustrates the preferred configuration of outlet valve 42. Outlet valve 42 has a generally cylindrical body 136 having substantially the same diameter as outlet valve channel 122 and a conical tip 138. Outlet valve 42 has a cylindrical portion 140 of larger diameter than cylindrical body 136. Portion 140 has a single channel 142 to minimize the volume of active compound retained in the area of spray nozzle 16. The single channel 140 further prevents air bubbles in and evaporation of the active compound.

Metered dose chamber 44 is in fluid communication with inlet valve channel 110, outlet valve channel 112 and shank channel 114; outlet valve channel 112 is in fluid communication with spray outlet 16; and inlet valve channel 110 is in fluid communication with active compound inlet 14. An inlet adapter 116 is provided between valve block 38 and active compound inlet 14 to permit fluid communication therebetween. Valve block 38 connects directly with spray nozzle 16. Inlet adapter 116 may be of any design that will permit fluid communication with medicament reservoir. Threads 146 are provided in inlet adapter 116 for receiving the container of active compound, not shown. A needle 144 is provided to puncture the collar of the container when the container is threaded into inlet adapter 116.

The operation of metered dose inhaler pump 10 is now described in detail. Active compound inlet 14 may be of any design that will permit an active compound container, not shown, to be connected thereto for delivering the active compound to metered dose chamber 44. In a normal condition of metered dose inhaler pump 10, trigger 18 is in a fully depressed position and held in such position by block portion 94 of cocking arm 30. In the normal condition, shank portion 106 of plunger 20 is urged into valve block 38 by block portion 94 of cocking arm 30 so that seat 78 is urged against valvetered dose inhaler pump 10 for usage, cocking arm 30 is pulled outwardly from housing 12 by pulling outwardly on cocking trigger 32 against the action of spring 34. When U-shaped channel 102 of cocking arm 30 is in vertical alignment with shaft portion 88 of trigger 18, spring 68 urges trigger 18 outwardly from housing 12 and perpendicularly to the movement of cocking arm 30. When trigger 18 is in its fully extended position, the interaction of U-shaped channel 102 and channel 50 of shaft portion 88 prevents further outward movement of trigger 18 and cocking arm 30. As trigger 18 is urged outwardly by spring 68, linkage 26 is rotated about pin 28 in a counter-clockwise direction, as viewed from the perspective of FIG. 2, by step portion 92 of trigger 18 acting upon leg 54. In turn, the foregoing rotation of linkage 26 urges plunger 20 outwardly from valve block 38 by the action of leg 52 against seat 78. The outward movement of plunger 20 creates a vacuum condition in metered dose chamber 44, inlet valve channel 110 and outlet nozzle 16. This vacuum condition causes both inlet valve 40 and outlet valve 42 to be urged inwardly toward metered dose chamber 44. The conical tip of outlet valve 42 is urged against the opening of the wall defined between metered dose chamber 44 and outlet valve channel 112, thereby fluidly sealing outlet valve channel 112 with respect to metered dose chamber 44 and preventing air or other gas or fluid from entering metered dose chamber 44 through spray outlet 16.

The vacuum condition further draws an amount of active compound from the active compound container, not shown, through inlet 14, inlet adapter 116 and inlet valve channel 110 and into metered dose chamber 44. Fins 48 of inlet valve 38 permit the active compound to be drawn past inlet valve 38. The amount of active compound drawn into metered dose chamber 44 is equal to the volume displacement of shank 106 of plunger 20. Thus, such volume displacement designed into metered dose inhaler pump 10 should be equal to the volume of the desired metered dose.

Once metered dose inhaler pump 10 is charged as described above, metered dose inhaler pump 10 is prepared to deliver a metered dose of the active compound to a person's respiratory tract. By depressing trigger 18, channel 50 is aligned with block portion 94, allowing cocking arm 30 to slide inwardly toward valve block 38. At such time, block portion 94 is urged against head 108 of plunger 20 by spring 34, and linkage 26 is rotated about pin 28 in a clockwise direction as viewed from the perspective of FIG. 2. Block portion 94 urging against head 108 of plunger 20 urges shank 106 of plunger 20 thereby pressurizing metered dose chamber 44, inlet valve channel 110 and outlet nozzle 16. Such pressurization urges inlet valve 40 and outlet valve 42 outwardly with respect to metered dose chamber 44. Conical tip of inlet valve 40 is urged against outlet nozzle 16 forming a fluid-tight seal, thereby preventing active compound from being ejected from active compound inlet 14.

Plunger 20 is urged into metered dose chamber 44 forcing active compound from metered dose chamber 44 through outlet nozzle 16 and delivering active compound to a person's respiratory tract. It will be appreciated that the dimensions of outlet nozzle 16 are such that outlet nozzle may deliver particle sizes suitable for inhalation treatment, which may be, for example, in a size range of 3 to 6 microns. Channel 142 of outlet valve 42 permit active compound to be delivered past outlet valve 42. The volume of active compound delivered to an operator's respiratory tract is equal to the volume displacement of metered dose chamber 44 by the action of shank 106. Metered dose chamber 44 has a diameter substantially equal to the diameter of shank 106 of plunger 20, so that the inward movement of shank 106 substantially fills and evacuates metered dose chamber 44, leaving substantially no void head space in metered dose chamber 44, inlet valve channel 110 or outlet nozzle 16.

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:

1. A metered dose inhaler pump, said pump comprising:
    a method dose chamber having an inlet for receiving a metered dose of an active compound and an outlet for dispensing the metered dose therefrom;
    an inlet valve being made of a resilient material disposed in said inlet, said inlet valve opens in response to a vacuum created in the chamber and being closed upon the cessation of vacuum;
    an outlet valve disposed in said outlet, said outlet being closed by said outlet valve when there is vacuum in said chamber and being open in response to pressure in said chamber to dispense said metered dose therefrom;
    means for creating a vacuum in said chamber for drawing therein said metered dose into said chamber via the inlet whilst the outlet remains closed by said outlet valve; and
    means for pressurizing said chamber which doses said inlet via the inlet valve and opens the outlet for dispensing said metered dose from said chamber to a person's respiratory tract through said outlet.

2. The pump according to claim 1, wherein said chamber has a volume substantially equal to said metered dose.

3. The pump according to claim 1, wherein said resilient material is a silicone elastomer.

4. The pump according to claim 1, wherein said means for creating a vacuum comprises a plunger in fluid communication with said metered dose chamber;
    and wherein when said plunger is translated from a first position to a second position, said plunger creates a vacuum in said chamber, opening said inlet valve by causing said inlet valve to change from a first state to a second state opening said inlet and drawing said metered dose into said chamber.

5. The pump according to claim 4, wherein said inlet valve comprises a cylindrical body having a plurality of fins extending radially outwardly from said cylindrical body, said metered dose passing between said fins when said metered dose is drawn from said container into said chamber.

6. The pump according to claim 4, wherein said pressurizing means comprises the plunger in fluid communication with said metered dose chamber;
    and wherein when said plunger is translated from the second position to the first position, said plunger pressurizes said chamber, opening said outlet valve to open said outlet and dispense said metered dose of said active compound from said chamber through said outlet whilst applying positive pressure to the inlet valve sealing the inlet.

7. The pump according to claim 6, further comprising means for biasing said plunger from said second position toward said first position.

8. The pump according to claim 7, wherein said biasing means comprises a helical spring.

9. The pump according to claim 6, wherein said outlet valve is made of a resilient material.

10. The pump according to claim 9, wherein said resilient material of the outlet valve is a silicone elastomer.

11. The pump according to claim 6, further comprising means for locking said plunger in said second position and a means for unlocking said plunger from said second position.

12. The pump according to claim 6, wherein said plunger substantially fills said chamber when translated from the first position to the second position and substantially evacuates said metered dose from said chamber when said plunger is translated from the second position to the first position.

13. A metered dose inhaler for delivering a metered dose of an active compound to a person's respiratory tract, said metered dose inhaler comprising:

an inlet for receiving a metered dose of an active compound and a spray outlet for dispensing said metered dose;

a mouthpiece adapted by size and configuration to couple with an oral orifice of said person;

a pump, said pump comprising means for drawing said metered dose and means for pressurizing said metered dose, said pressurizing means delivering said metered dose from said pump through the spray outlet to said person's respiratory tract through said mouthpiece;

wherein said pump further comprises a metered dose chamber in fluid communication with said inlet and said spray outlet, wherein said drawing means comprising an inlet valve disposed within said inlet and a plunger in fluid communication with said metered dose chamber, wherein when said plunger is translated from a first position to a second position, said plunger creates a vacuum in said metered dose chamber, opening said inlet valve and drawing said metered dose into said metered dose chamber, and an outlet valve disposed in said spray outlet which seals the spray outlet whilst the metered dose is drawn into the metered dose chamber wherein said outlet valve comprises a cylindrical body having a first diameter and a cylindrical portion extending from said cylindrical body, said cylindrical portion having a second diameter larger than said first diameter, said cylindrical portion having at least one longitudinal channel, said metered dose passing along said channel when said metered dose is delivered from said metered dose chamber to said person's respiratory tract.

14. The metered dose inhaler according to claim 13, wherein said mouthpiece is rotatably retractable into a housing of said metered dose inhaler.

15. The metered dose inhaler according to claim 13, further comprising a cover for encasing an unpressurized container which contains the active compound.

16. The metered dose inhaler according to claim 15, wherein said cover includes a portion which is transparent to permit visual inspection of the amount of active compound remaining in said container.

17. A pump for material, said pump comprising:

a chamber;

an inlet for receiving material which passes therethrough into said chamber;

an inlet valve disposed in said inlet being made of a resilient material, said inlet valve having a first state in which the valve engages and seals off said inlet by engagement therewith and a second state which, as a result of application pressure said inlet valve disengages said inlet so as to allow the material to pass thereby, whereupon upon cessation of pressure, due to resiliency of said inlet valve, the valve returns to said first state sealing off said inlet;

a spray outlet;

means for drawing said material into said chamber; and means for pressurizing said chamber for dispensing said material from said chamber via the spray outlet.

18. The pump according to claim 17, wherein said resilient material is a silicone elastomer.

19. The pump according to claim 17, wherein said means for drawing comprises a plunger in fluid communication with said chamber;

and wherein when said plunger is translated from a first position to a second position, said plunger creates a vacuum in said chamber, causing said inlet valve to change from a first state to a second state opening said inlet and drawing said material into said chamber.

20. The pump according to claim 19, wherein said means for pressurizing comprises an outlet valve disposed within said spray outlet and the plunger in fluid communication with said chamber;

and wherein when said plunger is translated from the second position to the first position, said plunger pressurizes said chamber, causing said outlet valve to open and eject said material from said chamber through said spray outlet whilst applying positive pressure to the inlet valve sealing the inlet.

21. The pump according to claim 20, further comprising means for biasing said plunger from said second position toward said first position.

22. The pump according to claim 20, wherein said biasing means comprises a helical spring.

23. The pump according to claim 20, wherein said outlet valve is made of a resilient material.

24. The pump according to claim 23, wherein said resilient material is a silicone elastomer.

25. The pump according to claim 20, further comprising means for locking said plunger in said second position and a means for unlocking said plunger from said second position.

26. The pump according to claim 20, wherein said plunger substantially fills said chamber with material when translated from the first position to the second position and substantially evacuates said material from said chamber when said plunger translates from the second position to the first position.

27. The pump according to claim 26, wherein said inlet valve comprises a cylindrical body having a plurality of fins extending radially outwardly from said cylindrical body so as to maintain said inlet valve centrally positioned in said inlet when in said first and second states and said material passing between said fins when said material is drawn into said chamber.

28. The pump according to claim 20, wherein said inlet valve comprises a cylindrical body having a plurality of fins extending radially outwardly from said cylindrical body so as to maintain said inlet valve centrally positioned in said inlet when in said first and second states and said material passes between said fins when said material is drawn into said chamber.

29. The pump according to claim 28, wherein said outlet valve comprises a cylindrical body having at least one channel extending radially inwardly into said cylindrical body, said material passing through said channel in said cylindrical body when said material is ejected from said chamber through said spray outlet.

30. The pump according to claim 20, wherein said outlet valve comprises a cylindrical body having at least one channel extending radially inwardly into said cylindrical body, said material passing through said channel in said cylindrical body when said material is ejected from said chamber through said spray outlet.

31. A pump comprising:

an inlet for receiving a metered dose of an active compound;

a spray outlet;

a metered dose chamber in fluid communication with said inlet and said outlet;

means for drawing said metered dose into said chamber;

means for pressurizing said metered dose chamber for delivering said metered dose from said chamber to a person's respiratory tract through said outlet, wherein said drawing means comprises an inlet valve within said inlet and a plunger in fluid communication with said metered dose chamber; wherein when said plunger is translated from a first position to a second position, said plunger creates a vacuum in said metered dose chamber, opening said inlet valve and drawing said metered dose into said metered dose chamber; and an outlet valve in said outlet wherein said outlet valve comprises a cylindrical body having a first diameter and a cylindrical portion extending from said cylindrical body, said cylindrical portion having a second diameter larger than said first diameter, said cylindrical portion having at least one longitudinal channel, said metered dose passing along said channel when said metered dose is pressurized for delivery from said metered dose chamber to a person's respiratory tract.

* * * * *

UNITED STATES PATENT AND TRADEMARK OFFICE
CERTIFICATE OF CORRECTION

PATENT NO. : 6,223,746 B1  
DATED : May 1, 2001  
INVENTOR(S) : Warren R. Jewett et al.

It is certified that error appears in the above-identified patent and that said Letters Patent is hereby corrected as shown below:

Column 6,
Line 12, the word "method" should be replaced with the word -- metered --.

Signed and Sealed this

Twenty-first Day of June, 2005

JON W. DUDAS
*Director of the United States Patent and Trademark Office*